(12) United States Patent
Fischer

(10) Patent No.: US 9,566,378 B2
(45) Date of Patent: Feb. 14, 2017

(54) METHOD FOR FILLING AND RINSING A SET OF BLOOD LINES

(71) Applicant: Fresenius Medical Care Deutschland GmbH, Bad Homburg (DE)

(72) Inventor: Max Fischer, Frankfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 164 days.

(21) Appl. No.: 14/626,555

(22) Filed: Feb. 19, 2015

(65) Prior Publication Data

US 2015/0165109 A1 Jun. 18, 2015

Related U.S. Application Data

(63) Continuation of application No. 12/227,220, filed as application No. PCT/EP2007/003767 on Apr. 27, 2007, now Pat. No. 8,980,094.

(30) Foreign Application Priority Data

May 11, 2006 (DE) ........................ 10 2006 022 122

(51) Int. Cl.
*A61M 1/36* (2006.01)
*A61M 1/34* (2006.01)
*A61M 1/16* (2006.01)

(52) U.S. Cl.
CPC ......... *A61M 1/3649* (2014.02); *A61M 1/1601* (2014.02); *A61M 1/3431* (2014.02); *A61M 1/3643* (2013.01); *A61M 1/3647* (2014.02); *A61M 2202/0413* (2013.01); *A61M 2205/33* (2013.01)

(58) Field of Classification Search
CPC A61M 1/1601; A61M 1/3431; A61M 1/3643; A61M 1/3647; A61M 1/3649; A61M 2202/0413; A61M 2205/33
USPC .......................................................... 210/141
See application file for complete search history.

(56) References Cited

U.S. PATENT DOCUMENTS

| | | | |
|---|---|---|---|
| 5,776,091 A | 7/1998 | Brugger et al. | |
| 5,776,345 A | 7/1998 | Truitt et al. | |
| 2002/0017489 A1 | 2/2002 | Utterberg | |
| 2002/0104800 A1 | 8/2002 | Collins et al. | |
| 2006/0079826 A1 | 4/2006 | Beden et al. | |

FOREIGN PATENT DOCUMENTS

| | | |
|---|---|---|
| DE | 4240681 | 6/1994 |
| DE | 10011208 | 9/2001 |

(Continued)

*Primary Examiner* — Dirk Bass
(74) *Attorney, Agent, or Firm* — Jacobson Holman, PLLC.

(57) ABSTRACT

A method for the filling and flushing of a blood tube set including a pump segment for a blood pump, an arterial line connected to an inlet of a dialyser, a venous line connected to an outlet of a dialyser, a substituate line connected to a substitute port and having a pump segment for a substitute pump, and a three-way connector connected to the arterial line, the venous line and a rinse port. The method includes the steps of opening the rinse port, filling and simultaneously flushing the arterial and venous lines with the substituate supplied from the substitute line via the substitute pump, while substituate is drained off via the rinse port, closing the rinse port, and circulating the substituate in the circuit of arterial line, dialyser and venous line by the blood pump.

13 Claims, 3 Drawing Sheets

(56) References Cited

FOREIGN PATENT DOCUMENTS

| EP | 0831945 | 5/2005 |
|----|---------|--------|
| WO | WO 96/40320 | 12/1996 |
| WO | WO 99/20376 | 4/1999 |

METHOD FOR FILLING AND RINSING A SET OF BLOOD LINES

This is a continuation application of co-pending application Ser. No. 12/227,220 filed on Nov. 12, 2008, which is a national stage of PCT/EP2007/003767 filed Apr. 27, 2007 and published in German, which has a priority of German application DE 10 2006 022 122.2 filed May 11, 2006, hereby incorporated by reference, the priority of which is hereby claimed.

BACKGROUND OF THE INVENTION

1. Field of the Invention

The invention relates to a method for the filling and flushing of a blood tube set, comprising a pump segment for a blood pump, an arterial line connected to an inlet of a dialysis machine and a venous line connected to an outlet of a dialysis machine, via a substituate line,

2. Description of the Related Art

Blood tube sets of this type are used in extracorporeal blood therapies, e.g. in hemodialysis, and form the extracorporeal blood circuit in this process. As a rule, disposable articles are used as the arterial and venous lines which are packed in a sterile manner and have to be filled and flushed prior to the treatment. This filling and flushing of the blood tube set is also called priming and serves to avoid the contact of blood with air in the extracorporeal therapy. In this connection, the blood tube system made as a disposable system is filled with substituate before the patient is connected for treatment so that the extracorporeal system is practically air-free after the priming. After the filling and flushing of the tube system, venous and arterial lines are typically connected to one another such that the substituate can circulate in this circuit of arterial line, dialyser and venous line until the patient is connected to the system. After the connection of the patient, the substituate is displaced by the inflowing blood such that a possible contact of the blood with air is reduced to a minimum.

Methods are known for the filling and flushing of blood tube sets using bags with a physiological solution and corresponding bags for the collection of the used solution. In this connection, a bag with saline solution is typically connected to the arterial line and the latter is filled. After the filling of the arterial line, the blood pump is now used to also fill and flush the venous line. For this purpose, the pump segment of the blood tube set, a tube section with specific properties, is inserted into the blood pump, typically a peristaltic pump or a roller pump, such that the blood pump can pump saline solution into the venous line via the pump segment.

To automate the filling and flushing process as much as possible, a method was proposed in EP 831 945 B1 in which a T connector is used to short-circuit the arterial line and the venous line for filling and flushing and to connect them to a bag to collect the used solution via the T connector. Furthermore, valves are necessarily provided in the proximity of the connector at the blood lines, that is at the arterial and venous lines, to control the filling and flushing process. First, in this process, the substituate is filled into the arterial line from a bag by the use of gravity. After the opening and closing of the corresponding valves, the liquid is thereupon filled from the arterial line into the venous line. After a further opening and closing of the corresponding valves, the substituate can then be circulated by the blood pump in the circuit of arterial line, dialyser and venous line. The attachment of the controllable valves to the blood tubing set is awkward and may not be forgotten in this process, additionally requires electrical and pneumatic connections and is prone to operating errors of the dialysis nurse, e.g. due to confusion or incorrect positioning of the valves. It is additionally necessary, before the start of the automatable procedure, to manually hang up a source with a sterile fluid (e.g. a bag with sterile saline solution) above the treatment machine, to pierce this source and connect it to the blood tubing set, with it having to be ensured that the valves have been correctly fitted beforehand and are closed. In addition, the valves must be controlled on the hardware side and software side for the automation of the valve actuation, with it simultaneously having to be ensured that none of the valves fail or are located in an incorrect closing position after the connection of the solution bag.

SUMMARY OF THE INVENTION

It is therefore the object of the present invention to make available a method for the filling and flushing of a blood tubing set which is safer in use and which can be carried out more simply, faster and more cost favorably.

In accordance with the invention, the object is solved by a method for the filling and flushing of a blood tubing set that includes a pump segment for a blood pump, an arterial line connected to an inlet of a dialyser and a venous line connected to an outlet of a dialyser, and a substituate line. The method includes the steps known per se for the connection of the arterial line to the venous line and for the connection of these two lines to a rinse port, connection of the substituate line to a substituate port, opening of the rinse port, filling the arterial and venous lines, flushing the arterial and venous lines, closing of the rinse port, and circulation of the substituate in the circuit of arterial line, dialyser and venous line by the blood pump. According to the present invention, however, the filling and/or the flushing of the arterial and venous lines take/takes place simultaneously, with substituate being supplied from the substituate line. The pump segment of the blood tubing set is naturally inserted into the blood pump before the use thereof.

It is in particular possible with this method to dispense with the attachment of valves to the blood tubing set which would have to control the filling or flushing of the arterial line and the subsequent filling or flushing of the venous line. The error sources associated with the attachment of these valves in operation are thus precluded. In addition, the simultaneous filling and/or flushing of the arterial and venous lines permit/permits a faster filling and flushing process since different method steps can be dispensed with. In addition, the method can also be automated more easily and the time which a dialysis nurse requires to fill and flush the blood tubing set is minimized. The blood tubing set is moreover thus favorable in price and does not have to be changed during the process. In addition, the process can be carried out completely at the treatment machine and be completely concluded even before the connection of the patient so that, as a rule, the patient can be absent during the preparation of the treatment machine.

The interfaces for the blood tubing set are the substituate port, via which substituate is introduced into the substituate line, and the rinse port, via which consumed substituate can be drained off again. Both the substituate port and the rinse port typically have valves with which they can be closed and opened for the application of the process.

The filling and the flushing advantageously form one continuous process in the method in accordance with the invention. In particular no interruption of the fluid flow thereby results, whereby the otherwise present risk is avoided that foam is formed due to a temporary interruption of the inflowing fluid flow as a result of air bubble transport. Not only arterial and venous lines are filled or flushed simultaneously in this connection, but this filling and flushing process also takes place continuously. In addition to the just-mentioned increase in safety, this also allows a simpler automation since in particular the use of valves at the blood tubing set can be dispensed with.

The filling and the flushing take place further advantageously by the same process here. It is thereby not necessary to switch separately between the filling and flushing process so that the control effort or operating effort for the method is reduced and safety is increased.

The simultaneous filling and/or flushing of the arterial and venous lines advantageously takes place in that the blood pump transports substitute in the blood tubing set while substitute is simultaneously supplied from the substitute line. It is thus only necessary to use already existing components of the blood tubing set to control the filling process and/or flushing process. The substitute from the substitute line is supplied into the blood tubing set, while the blood pump ensures that both the arterial and venous lines are flowed through by substitute. It is thereby possible to dispense with valves and for both the arterial and the venous lines to be filled or flushed simultaneously.

The blood pump advantageously transports an amount n of substitute during the filling and/or flushing process, with an amount m+n of substitute being supplied to the line to the blood pump on the suction side from the substitute line. The blood pump thereby pumps a portion n of the substitute supplied from the substitute line through the pressure-side part of the blood tubing set, while the suction-side part of the blood tubing set is flowed through directly by the remaining amount m of the substitute from the substitute line from the infeed of the substitute line. In this method, both parts of the blood tubing set are therefore flowed through simultaneously in parallel and in the same direction, with both substitute flows coming together again at the rinse port after the filling of the blood tubing set and being drained away from there.

In this manner, a simple method results with which the blood tubing set can be filled and flushed safely and fast, with only the amounts having to be controlled which are transported by the blood pump or which are supplied from the substitute line.

The blood pump advantageously runs backward in this process. In particular when the pump segment for the blood pump is integrated in the arterial line, the blood pump thus pumps substitute directly through the arterial line to the rinse port, while the remaining substitute flows through the dialyser and the venous line and then combines in the rinse port with the substitute pumped directly from the blood pump.

Alternatively, the blood pump can circulate at least some of the substitute in the circuit of arterial line, dialyser and venous line during the simultaneous filling and/or flushing of the arterial and venous lines, while substitute is additionally supplied from the substitute line. The substitute therefore no longer flows in parallel through the arterial and venous lines, but circulates through them, while the substituate added into the blood tubing set at the connection of the substitute line flows off again at the rinse port. This also allows a simple and safe method for the filling and flushing of the blood tubing set. It is in particular not decisive with this method how much substitute is supplied from the substitute line. The blood pump sucks substitute of the amount n into the extracorporeal blood circuit at the connection site between arterial and venous lines and circulates the substitute there so that a particularly effective flushing results. Fresh substitute of the amount m flows in via the substitute line and thus continuously dilutes the used substitute so that the substitute in the amount m+n flows in the region after the inlet of the substitute line, said substitute again flowing out partially, and indeed with the amount m, via the rinse port. In this connection, less substitute can in particular be supplied via the substitute line than is circulated in the extracorporeal blood circuit by the blood pump so that a particularly effective filling and flushing results. The addition site for the amount m of substitute advantageously lies at the pressure-side line of the forwardly running blood pump.

The pump segment for the blood pump is advantageously arranged in the arterial line in the method in accordance with the invention. The substitute is furthermore advantageously supplied between the blood pump and the dialyser, at the pre-dilution port of the blood tubing set. Freshly added substitute thus first flows at least partially through the dialyser, whereby the latter is cleaned particularly effectively.

If the blood pump runs backward, the amount n of substitute pumped by the blood pump is thereby transported through the arterial line in the direction of the rinse port. The amount m+n of substitute supplied from the substitute line into the pre-dilution port of the blood tubing set in this process is therefore partially pumped into the arterial line by the blood pump, while the rest flows through the dialyser and the venous line.

In the second method alternative, the blood pump runs forward, in contrast, and sucks substitute out of the venous line into the arterial line at the connection between the venous and arterial lines and pumps it further through the dialyser and back into the venous line. The substitute is supplied via the pre-dilution port and mixes with the already circulating substitute. The substitute is drained off again at the rinse port as soon as the blood tubing set is filled to the same degree as the substitute is supplied at the pre-dilution port.

While the method in accordance with the invention can also be operated while using bags for the filling and flushing and corresponding bags for the collection of the used solution, it is used particularly advantageously in a system with integrated substitute preparation. The substitute port and the rinse port are part of this system, with the fresh substitute being made available via the substitute port, while the used substitute is led back for preparation via the rinse port. This in particular means that the blood tubing set is integrated into a circuit.

Both ports furthermore advantageously have a valve at the machine side so that the valves do not have to be components of the blood tubing set. With such a system with integrated substitute preparation, it is in particular no longer necessary to make use of bags so that the costs for the procuring, storing, use and disposal of these bags are avoided. A particular advantage of the method in accordance with the invention in particular consists of the fact that existing systems with integrated substitute preparation do not have to be changed hardware-wise to use the method in accordance with the invention. Only a new software control is required so that existing systems can be fitted with the method in a simple manner.

The control of the rinse port and of the blood pump advantageously takes place automatically in the method in accordance with the invention, Only the connections of the tubing set have to be established at the start in the method in accordance with the invention, while the total filling and flushing process takes place automatically. A lot of work is thereby saved for the dialysis nurse, with error possibilities due to incorrect operation simultaneously being precluded.

The substitute is furthermore advantageously supplied via a substitute pump. This permits a precise control of the added amount so that the filling and the flushing can take place in an extremely controlled manner.

The control of the substitute pump advantageously takes place automatically so that no manual operating steps are required here either so that error sources associated therewith are precluded and time can be saved.

A pump segment for the substitute pump is furthermore advantageously integrated in the substitute line. In particular with a connection to a system with integrated substitute preparation, this system does not have to be changed hardware-wise by this since all the components required for the operation of the method are available outside the system.

The control of the substitute pump also advantageously takes place automatically. For this purpose, the system with integrated substitute preparation should advantageously be fitted with new software which controls the cooperation in accordance with the invention of the substitute port, the rinse port, the blood pump and the substitute pump. No further changes, in particular on the hardware side, are necessary so that existing systems can be fitted with the new method in a simple manner.

A T connector is advantageously used for the connection of the arterial line, the venous line and the rinse port so that this connection can be established in a simple and reliable manner.

While the substitute is drained off via the rinse port with the simultaneous flushing of the arterial and venous lines, it is also equally possible to drain substitute off via the dialyser during the flushing or the circulation of the substituate.

The present invention furthermore comprises a blood tubing set which includes a pump segment for a blood pump, an arterial line connectable to an inlet of a dialyser and a venous line connectable to an outlet of a dialyser as well as a substitute line and a connector, with the connector being connectable to the arterial line, the venous line and a rinse port, with a pump segment for the substitute pump being integrated in the substitute line. The connection to a system with integrated substitute preparation is in particular possible by the integration of the pump segment for the substitute pump in the substitute line without changing said system hardware-wise. The method in accordance with the invention for the filling and flushing of the blood tubing set can thus be realized particularly simply and cost favorably using the blood tubing set in accordance with the invention.

Embodiments of the present invention will now be described in more detail with reference to the drawings. There are shown;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
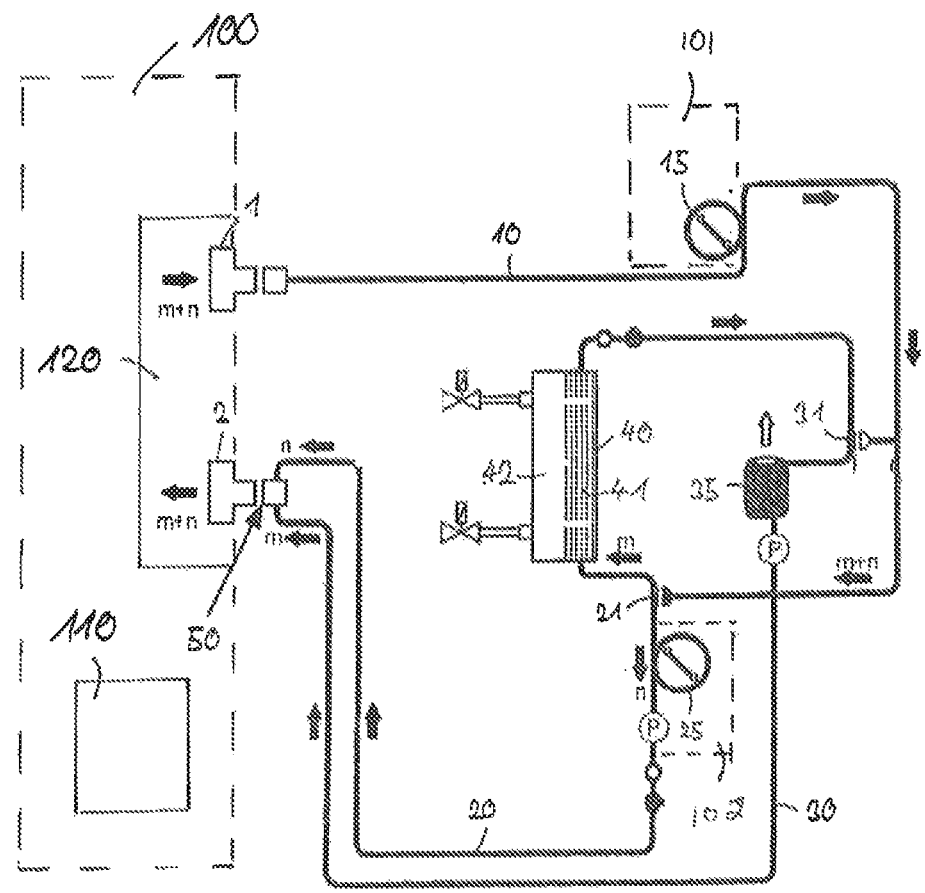
FIG. 1: a first embodiment of the filling and flushing process in accordance with the invention.

A first embodiment of the invention is shown in FIG. 1. The extracorporeal blood treatment system 100, 101, 102 with integrated substitute preparation unit 120 comprises the substitute port 1 and the rinse port 2 at the machine side. Fresh substitute is dispensed into the blood tubing set via the substitute port 1, while used substitute is drained off and prepared via the rinse port 2.

The actual blood tubing set consists of an arterial line 20 and a venous line 30. The pump segment for the blood pump 25 is located in the arterial line 20; the air separator 35 is located in the venous line 30. The dialyser 40 comprises two chambers, a dialysate chamber 42 for the flushing fluid and a blood chamber 41 via which the dialyser 40 is integrated into the extracorporeal blood circuit. For this purpose, the arterial line 20 is connected to the inlet of the blood chamber 41 of the dialyser 40 behind the blood pump 25. The outlet of the blood chamber 41 is connected to the venous line 30, with fluid flowing out of the blood chamber 41 first entering into the air separator 35 to separate any air bubbles which may occur. The pre-dilution port 21 is located in the arterial line 20 between the blood pump 25 and the inlet of the blood chamber 41. The post-dilution port, which is, however, not used in the present embodiments of the method in accordance with the invention, is located in the venous line 30 between the outlet of the blood chamber 41 and the air separator 35. The substitute line 10 is connected to the pre-dilution port and has a pump segment for a substituate pump 15.

The substitute line 10 is connected to the substitute line port 1 of the blood treatment system for the carrying out of the method in accordance with the invention for the filling and flushing of the blood tubing set. The ends of the venous line 30 and of the arterial line 20 at the patient side are short circuited via a T connector 50 and are connected to the rinse port 2 of the blood treatment system. Both substitute port 1 and rinse port 2 are open.

In the method variant shown in FIG. 1, an amount m n substitute is sucked in by means of the substitute pump 15 via the substitute port 1 and is fed via the pre-dilution port 21 into the arterial line 20 between the blood pump 25 and the inlet of the dialyser 40. The blood pump 25 runs in the reverse direction of rotation and pumps an amount n of substitute directly through the arterial line 20 to the T connector 50 and thus into the rinse port 2. The remaining portion of the substitute, that is the amount m, necessarily flows through the blood chamber 41 of the dialyser 40 and then through the air separator 35 before this partial flow likewise flows through the venous line 30 into the T connector 50 and thus into the rinse port 2.

In this embodiment, the arterial line and the venous line are therefore flowed through in parallel and simultaneously by two partial flows during flushing. The partial flows separate at the pre-dilution port 21 and combine again at the rinse port from where they are supplied to the substitute preparation of the blood treatment system. In this manner, both the venous and the arterial lines can be filled simultaneously, with only the blood pump 25 and the substitute pump 15 having to be controlled by control unit 110 for the control of this process, without further valves having to be provided at the blood tubing set. The filling and flushing process thus also take place in a single workstep since the substituate from the substituate port 1 first fills the blood tubing set and then flushes it with the pumps continuing to run, with the used substituate flowing off via the open rinse port 2.

Figure 2:
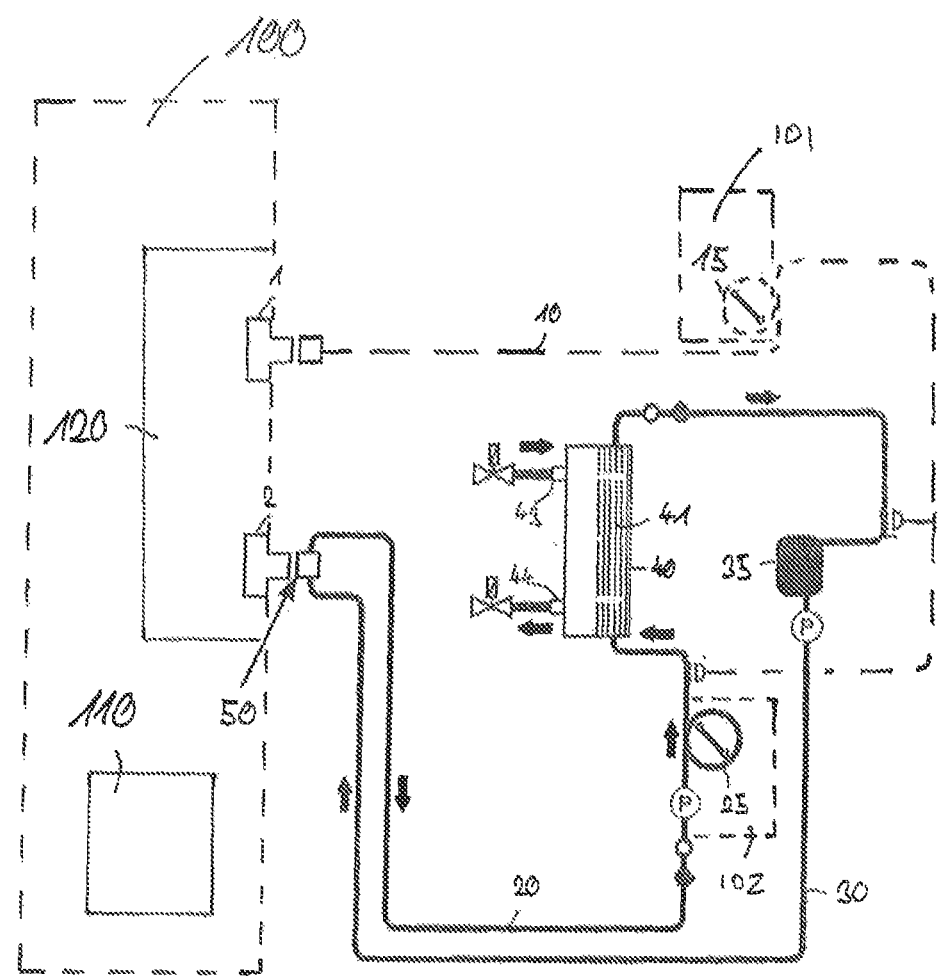
FIG. 2: a first embodiment of the circulation in accordance with the invention.

In FIG. 2, both the substituate port 1 and the rinse port 2 are closed so that substituate no longer flows into the blood tubing system and also no longer flows off. In this pre-circulation operation, the blood pump 25 now operates in its usual direction of rotation and thus transports forwardly. The substituate now circulates in the blood tubing set in the circuit in the order dialyser 40, air separator 35, venous patient line 30, T connector 50, arterial patient line 20, before it again enters the blood pump 25 and is pumped on from there. The transition from flushing operation to pre-circulation operation is thus also possible, without connections having to be changed or valves at the blood tubing set having to be opened or closed. The control is therefore in turn only possible via the opening and closing of the ports on the machine side and via the control of the pumps.

Figure 3:
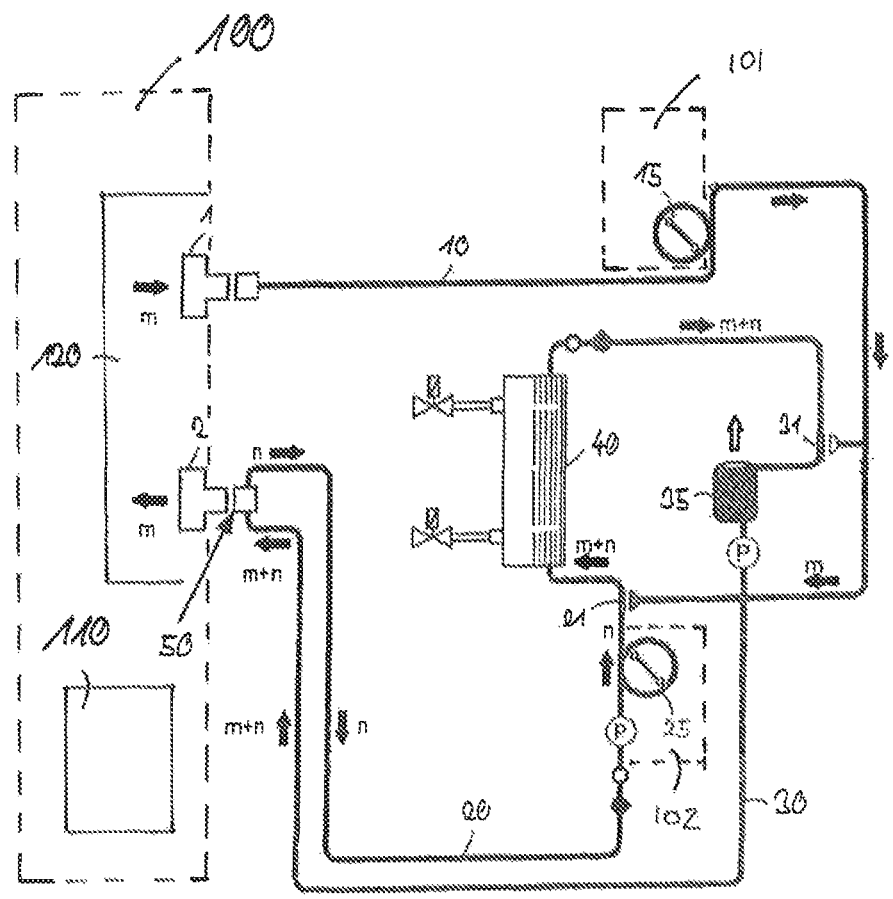
FIG. 3: a second embodiment of the filling and flushing process in accordance with the invention.

FIG. 3 now shows a second embodiment of the method in accordance with the invention for the filling and flushing of the blood tubing set. The design and the connection of the blood tubing set is identical to the first embodiment, but the filling and flushing process now takes place with the fluid flow circulating in the blood tubing set.

In this process, with the substituate pump 15 running, an amount m of substituate is permanently pumped into the pre-dilution port 21 of the blood tubing set. The same amount m of used substituate is permanently dispensed via the T connector via the rinse port, while the blood pump 25 operates in the forward direction in the arterial line 20 and pumps an amount n of substituate. In the pre-dilution port 21, the substituate flows from the blood pump 25 and from the substituate line 10 therefore combine to form a substituate flow of the amount m n which flows via the blood chamber 41 of the dialyser 40 on into the air separator 35 and from there via the venous line 30 to the T connector 50. At the T connector 50, an amount m of used substituate now flows off via the rinse port while the rest of the fluid flow of the amount n is sucked into the arterial line 20 by the blood pump 25. In this method variant, the arterial line 20 and the venous line 30 are therefore simultaneously flowed through in series. The substituate flows through the blood tubing set in the order dialyser 40, air separator 35, venous patient line 30, T connector 50, arterial patient line 20, to then move again to the blood pump 25 and be pumped on from there.

To bypass the pre-circulation, it is only necessary to switch off the substituate pump 15 and to close the substituate port 1 and the rinse port 2. The blood pump 25 simply continues to run and circulates the substituate in the blood tubing set as already shown in FIG. 2. Not only the filling and the flushing of the blood tubing set takes place in one process by this method, but the flushing and the pre-circulation following it also take place seamlessly.

The blood pump 25 is stopped to end the pre-circulation. The arterial line 20 and the venous line 30 are then disconnected from the connector 50 so that the patient can be connected to these lines.

The changes to use the method in accordance with the invention for the filling and flushing of the blood tubing set which have to be made to existing blood treatment systems are limited to the use of the special T connector 50, which can be made as a cost-favorable disposable article, and of the integrated substituate pump as well as the change of the control program of the treatment machine, with no new components having to be taken into account or controlled. The changes are therefore limited to changes to the software. The necessity of an additional disturbing electrical cabling associated with costs is in particular not present.

Furthermore, the advantage results that the blood tubing set is completely machine-controlled by control unit 110 and filled and flushed in a controlled manner and that moreover a transition is made to the pre-circulation of the substituate without interruption. The filling and flushing in particular takes place continuously and without any interruption of the fluid flow, which additionally increases safety, The error sources associated with manual treatment steps are thus precluded.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An extracorporeal blood treatment machine comprising:
   a substituate port,
   a rinse port,
   a blood pump,
   a substitutate pump and
   a control unit comprising software to control the substituate port, the rinse port, the blood pump and the substituate pump,
   wherein a blood tubing set that includes a pump segment for the blood pump, an arterial line connected to an inlet of a dialyser, a venous line connected to an outlet of the dialyser, a substituate line having a pump segment for the substituate pump, and a three-way connector connected to the arterial line and the venous line is connectable to the blood treatment machine for filling and flushing by connecting the three-way connector to the rinse port and the substituate line to the substituate port;
   said control unit being programmed to automatically control the substituate port, the rinse port, the blood pump and the substituate pump during filling and flushing such that said rinse port is opened for simultaneous filling of the arterial and the venous lines and simultaneous flushing of the arterial and the venous lines, with substituate being supplied by control of the substituate pump by the control unit in an amount of m+n via the substituate line to a suction-side of the blood pump while the blood pump is controlled by the control unit to transport an amount n, drawn from the amount m+n of the substituate supplied by the substituate pump, through the arterial line or the venous line to the three-way connector such that, simultaneously with transport of the amount n, an amount m of substituate flows to the three-way connector through the other of the arterial line or the venous line in another direction, while an amount m+n of substituate is drained off via the rinse port that is controlled by the control unit to be open, and said rinse port being controlled to close for circulating of the substituate in the circuit of arterial line, dialyser, and venous line by operation of the blood pump.

2. The machine in accordance with claim 1, wherein the filling and the flushing represent a continuous process.

3. The machine in accordance with claim 1, wherein the blood pump is controlled by the control unit to run backwardly during the filling and flushing.

4. The machine in accordance with claim 3, wherein the substitute pump is controlled by the control unit to operate simultaneously with the blood pump and, in pumping the amount m+n, the substituate pump pumping more substituate than the blood pump which only pumps the amount n of the amount m+n, necessitating the flow of the amount m into the other of the arterial line or the venous line when simultaneously filling and flushing the arterial and venous lines.

5. The machine in accordance with claim 1, wherein the blood pump is connectable to the arterial line and the substituate is supplied between the blood pump and the dialyser.

6. The machine in accordance with claim 1, comprising an integrated substitute preparation unit, wherein the substituate port and the rinse port form part of the substituate preparation unit.

7. The machine in accordance with claim 1, wherein the substituate pump and the blood pump are controlled by the control unit such that substituate is drained off via the dialyser with the simultaneous flushing of the arterial line and of the venous line or during circulation.

8. An extracorporeal blood treatment machine comprising
a substituate port,
a rinse port,
a blood pump,
a substitutate pump and
a control unit comprising software to control the substituate port, the rinse port, the blood pump and the substituate pump,
wherein a blood tubing set that includes a pump segment for the blood pump, an arterial line connected to an inlet of a dialyser, a venous line connected to an outlet of the dialyser, a substituate line having a pump segment for the substituate pump, and a three-way connector connected to the arterial line and the venous line is connectable to the blood treatment machine for filling and flushing by connecting the three-way connector to the rinse port and the substituate line to the substituate port;
said control unit being programmed to automatically control the substituate port, the rinse port, the blood pump and the substituate pump during filling and flushing such that said rinse port is opened for simultaneous filling of the arterial line and the venous line and simultaneous flushing of the arterial line and the venous line with substituate being supplied from the substituate pump via the substituate line, said blood pump being controlled by the control unit to pump substituate in an amount n for circulation in the circuit of arterial line, dialyser and venous line, while the substituate pump is controlled by the control unit to supply an amount m of additional substituate via the substituate line downstream of the blood pump in the circuit of the arterial line, dialyser and venous line, such that an amount n+m of substituate flows through the dialyser, an amount m of substituate being drained off via the rinse port controlled by the control unit to be open and an amount n not drained off flowing back to the blood pump for circulation, and said rinse port being controlled to be closed for circulating of the substituate in the circuit of arterial line, dialyser, and venous line by operation of the blood pump.

9. The machine in accordance with claim 8, wherein the filling and the flushing represent a continuous process.

10. The machine in accordance with claim 9, wherein the blood pump is controlled by the control unit to run in the forward direction during the filling and flushing.

11. The machine in accordance with claim 8, wherein the blood pump is connectable to the arterial line and the substituate is supplied between the blood pump and the dialyser.

12. The machine in accordance with claim 8, comprising an integrated substituate preparation unit, wherein the substituate port and the rinse port form part of the substituate preparation unit.

13. The machine in accordance with claim 8, wherein the substituate pump and the blood pump are controlled by the control unit such that substituate is drained off via the dialyser with the simultaneous flushing of the arterial line and of the venous line or during circulation.

* * * * *